United States Patent [19]

Andersen et al.

[11] Patent Number: 4,556,673
[45] Date of Patent: Dec. 3, 1985

[54] USE OF PHTHALYLTAURINE SULFONAMIDE DERIVATIVES IN TREATING EPILEPSY AND ARRYTHMIA

[76] Inventors: Lars H. Andersen, Linnankoskig. 10, Helsinki, Finland, SF-00250; Leif A. Hildén, Skogvägen 14, Nickby, Finland, SF 04130

[21] Appl. No.: 342,018
[22] PCT Filed: May 22, 1981
[86] PCT No.: PCT/FI81/00037
 § 371 Date: Jan. 11, 1982
 § 102(e) Date: Jan. 11, 1982
[87] PCT Pub. No.: WO81/03492
 PCT Pub. Date: Dec. 10, 1981

[30] Foreign Application Priority Data

Jun. 6, 1980 [SE] Sweden ................. 8004261

[51] Int. Cl.$^4$ ............ A61K 31/40; C07D 209/48; C07D 403/12
[52] U.S. Cl. ............ 514/414; 514/417; 548/465; 548/467
[58] Field of Search ........... 548/465, 477; 424/274

[56] References Cited

U.S. PATENT DOCUMENTS

2,184,279 12/1939 Christiansen .............. 260/556
4,066,762  1/1978 Dunn ...................... 424/246

FOREIGN PATENT DOCUMENTS

1254414 11/1971 United Kingdom ............ 548/477

OTHER PUBLICATIONS

Chem. Abstracts Subject Index 1967–71, pp. 30082S–30083S.

Greene, Theodora, Protective Groups in Organic Synthesis, John Wiley, New York (1981) pp. 265–267.
Naito, Shunichi; "Aminoethanesulfonyl Derivatives," Chem. Abst. 76: 140209u (1972).
J. F. Mead et al., J. Organic Chemistry 12, (1947) 295.
D. A. Berges et al., J. Heterocyclic Chemistry, 15, (1978), 981.

Primary Examiner—Donald G. Daus
Assistant Examiner—G. M. Hendricks
Attorney, Agent, or Firm—McAulay, Fields, Fisher, Goldstein & Nissen

[57] ABSTRACT

The invention relates to taurine derivatives with the chemical structure:

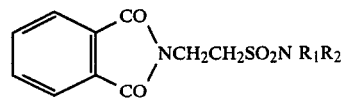

where
$R_1 = H$
$R_2 =$ a lower alkyl group with up to 4 carbonatoms or an acetyl group
or where

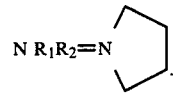

These compounds were found in pharmacological studies to have qualities which make them useful as drugs.

4 Claims, No Drawings

USE OF PHTHALYLTAURINE SULFONAMIDE DERIVATIVES IN TREATING EPILEPSY AND ARRYTHMIA

The present invention relates to taurine derivatives, their production, and their use in drugs. The compounds are phthalyltaurine sulfonamides with the chemical structure:

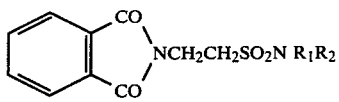

where
$R_1 = H$,
$R_2 =$ a lower alkyl group with up to 4 carbonatoms or an acetyl group,
or where

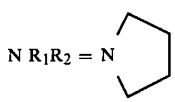

The new compounds synthesized by us are:
2-Phthalimidoethanesulfone methylamide
2-Phthalimidoethanesulfone ethylamide
2-Phthalimidoethanesulfone n-propylamide
2-Phthalimidoethanesulfone isopropylamide
2-Phthalimidoethanesulfone n-butylamide
2-Phthalimidoethanesulfone pyrrolidide.

In addition, we have synthesized the following compounds previously described in the literature: 2-phthalimidoethane sulfonamide, 2-phthalimidoethanesulfone dimethylamide, 2-phthalimidoethanesulfone tertbutylamide and 2-phthalimidoethane sulfonylacetamide, which were found in pharmacological studies to have the same good drug qualities as the present new compounds.

Taurine, 2-aminoethanesulfonic acid, occurs in rich amounts in human tissues. Particularly high concentrations are found in the spleen, muscles, and brain (Jacobsen J. C. & Smith L. J., Jr Physiol. Rev 48, 424–511, 1968). There is good reason to believe that taurine acts as an inhibitory neurotransmitter in the central nervous system. The role of taurine is not yet definitely clarified. Decreased taurine concentrations have been observed in some cases of epilesy. Taurine has been found to have a direct central anticonvulsive effect in several types of experimental epilepsy. A Barbeau & Donaldson (Arch. Neurol. 30, 50–58, 1974) and R. Takahaski & Y. Nakane (Taurine and Neurological Disorders, 375–385, 1978) have demonstrated an antiepileptic action of taurine in the treatment of epileptic patients.

As taurine is an extremely hydrophilic compound, it seems unlikely that administered external taurine could penetrate into the brain in large enough amounts to produce a direct anticonvulsive effect in epileptic patients with intact bloodbrain barrier. Thus, to reach the brain in sufficient quantities, taurine must be given intracerebrally.

The present taurine derivatives are considerably more lipophilic than taurine, but they still have the same anticonvulsive properties. The synthesized compounds have been shown in pharmacological tests to have a good anticonvulsive effect. Theoretically, thus, it appears that they could be of value in antiepileptic therapy. The compounds have also been found antiarrhythmically active.

The pharmacological actions of taurine derivatives are only sparingly described i the literature. J. F. Mead & J. B. Koepfli (J. Org. Chem. 12, 295–297, 1947) have synthesized pantoyl taurinamide and 2-phthalimido-N-bimethylathane sulfonamide and studied their effect in malaria. R. Winterbottom et al. (J.A.C.S. 69, 1393–1401, 1947) synthesized 2-phthalimidoethane sulfonamide and 2-phthalimidoethanesulfone dimethylamide and studied their antibacterial properties, which did not come up to expectations.

J. W. Griffin & D. H. Hey (J. Chem.Soc. 3334–3340, 1952) describe the synthesis of 2-phthalimidoethanesulfonyl acetamide.

Of more recent publications the following could be mentioned: The European patent application no. 0 002 675 (P. H. Chakrabarti, GAF Corporation, 1979) relates to the production of salt-free N-acyl taurines used as surface-active agents. The French patent publication no. 2412523 (P. Reynard, 1979) relates to injectable forms of N-acetyl taurine, which in pharmacological tests were found to penetrate the bloodbrain barrier.

Gamma-L-glutamyl taurine, whose effect resembles that of vitamin A, has been tested by L. Feuer (Comp. Biochem. Physiol. 62 A, 995–997, 1979) among others. Liisa Ahtee et al. (Proc. B.P.S., Brit. J. Pharmacol. 480P, 1979) have studied the effect of various taurine derivatives on the central nervous system of mice after intraperitoneal administration. They found that N-pivaloyl taurine penetrated the blood-brain barrier.

The present invention is characterized by that the new compounds with the above-described pharmacological properties are synthesized (A) by conversion of phthalimidoethane sulfonylchloride with a primary amine through the following reaction:

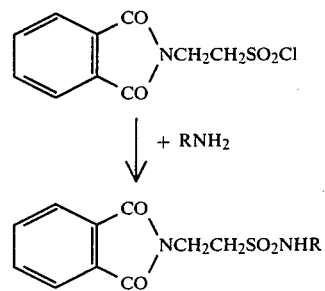

where R is a methyl-, ethyl-, n-propyl-, isopropyl- or n-butylgroup (B) by conversion of phthalimidoethane sulfonylchloride with a secondary amine or pyrrolidine:

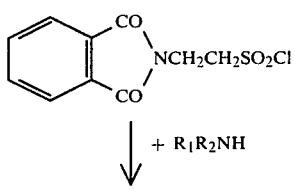

-continued

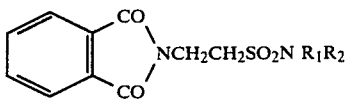

where

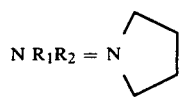

(C) by alkylation of phthalimidoethane sulfonamide with known alkylating agents such as alkyl halogenides, dialkyl sulfate, etc.:

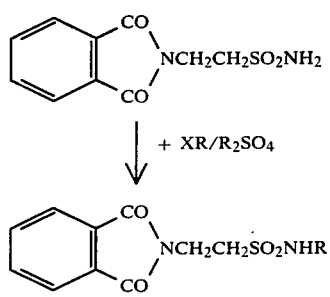

where

X is a halogen,

R is a methyl-, ethyl-, n-propyl-, isopropyl- or n-butylgroup.

In addition, 2-phthalimidoethane sulfonamide, 2-phthalimidoethanesulfone dimethylamide, 2-phthalimidoethanesulfone tert-butylamide and 2-phthalimidoethanesulfonyl acetamide, which in pharmacological screening tests were found to have the same valuable properties as the present new compounds, were synthesized by a previously known method.

The purity of the compounds was tested by thinlayer chromatography. Elementary analysis of all the new compounds was performed, and their IR, UV and NMR spectra were recorded.

The following examples illustrate the invention in more detail:

EXAMPLE 1

2-Phthalimidoethanesulfone methylamide 13.70 g of phthalimidoethanesulfonylchloride is dissolved in 200 ml of methylene chloride. Under stirring and cooling to 15°–20° C., a current of gaseous methylamine is conducted through the solution for 0.5 h. The solvent is evaporated, water is added to the solution, and the precipitate formed is filtered off, washed with water and dried. Recrystallization from ethanol yields 10.91 g of sulfonamide, m.p. 142°–144° C.

The yield is 81% of the theoretical. Calculated for $C_{11}H_{12}N_2O_4S$: C=49.2, H=4.5, N=10.4, S=12.0, Obtained: C=49.3, H=4.4, N=10.4, S=12.0.

EXAMPLE 2

2-Phthalimidoethanesulfone methylamide

Another method of preparing 2-phthalimidoethanesulfone methylamide is by a two-phase reaction in the following way:

To a mixture of 2.74 g of phthalimidoethane sulfonylchloride and 1.36 g of methylamine hydrochloride in 30 ml of methylene chloride there is added 7 ml of saturated potassium carbonate solution, and the mixture is stirred thoroughly for 10 minutes, after which the organic phase is separated, washed with water and dried, and the clear solution is evaporated. Yield: 2.14 g=80% of theoretical; m.p. 142°–144° C.

EXAMPLE 3

2-Phthalimidoethanesulfone ethylamide 8.21 g of 2-phthalimidoethane sulfonylchloride is dissolved in 70 ml of methylene chloride, and 3.00 g of ethylamine in 10 ml of methylene chloride. The solutions are cooled to 4° C., combined, and stirred for 30 minutes; the temperature rises to approximately 27° C. After evaporation of the reaction mixture, water is added and the precipitate formed is filtered off and washed. Recrystallization from ethanol yields 6.31 g of sulfonamide, melting at 111°–114° C.; 79% of theoretical yield.

Calculated for $C_{12}H_{14}N_2O_4S$: C=51.2, H=5.0, N=9.9, S=11.4; obtained C=51.2, H=5.0, N=10.0, S=11.4.

EXAMPLE 4

2-Phthalimidoethanesulfone ethylamide

To a mixture of 2.74 g of phthalimidoethane sulfonylchloride and 1.23 g of ethylamine hydrochloride in 30 ml of methylene chloride there is added 7 ml of saturated potassium carbonate solution and the mixture is stirred thoroughly for 10 minutes, after which the organic phase is separated, washed with water, dried and evaporated. Recrystallization yields 2.15 g of a product melting at 111°–114° C. The yield is 76% of the theoretical.

EXAMPLE 5

2-Phthalimidoethanesulfone n-propylamide 8.22 g of 2-phthalimidoethane sulfonylchloride, 4.02 g of n-propylamine hydrochloride, 120 ml of methylene chloride and 21 ml of saturated potassium carbonate solution are prepared as in Example 2. Recrystallization from 90% ethanol and ethylacetate yields 4.87 g of sulfonamide, m.p. 112°–114° C. Yield 55% of theoretical.

Calculated for $C_{13}H_{16}N_2O_4S$: C=52.7, H=5.4, N=9.5, S=10.8; obtained C=52.9, H=5.4, N=9.5, S=10.8.

EXAMPLE 6

2-Phthalimidoethanesulfone isopropylamide

To 21 ml of saturated potassium carbonate solution there is added 45 ml of methylene chloride and 2.48 g of isopropylamine. 8.22 g of 2-phthalimidoethane sulfonylchloride is dissolved in 45 ml of methylene chloride and added to the reaction mixture. Recrystallization from ethanol yields 8.01 g of sulfonamide, m.p. 137°–139° C.; 90% of theoretical yield.

Calculated for $C_{13}H_{16}N_2O_4S$: C=52.7, H=5.4, N=9.5, S=10.8; obtained C=53.0, H=5.5, N=9.5, S=10.9.

EXAMPLE 7

2-Phthalimidoethanesulfone n-butylamide

To a mixture of 2.40 g of phthalimidoethane sulfonylchloride and 25 ml of methylene chloride there is added 1.00 g of n-butylamine and immediately afterwards, under stirring, 20 ml of 2.8N sodium carbonate solution. After this the mixture is stirred for 10 minutes and the organic phase is separated, washed with water, dried, and evaporated. Recrystallization from cyclohexane yields 1.85 g, m.p. 71°–73° C. Yield 68% of theoretical.

Calculated for $C_{14}H_{18}N_2O_4S$: C=54.2, H=5.8, N=9.0, S=10.3; obtained C=52.3, H=5.8, N=9.1, S=10.3.

EXAMPLE 8

2-Phthalimidoethanesulfone tert-butylamide 36.1 g of 2-phthalimidoethane sulfonylchloride in 98.2 ml of pyridine is cooled to 0°–3° C. 4.3 g of tert-butylamine is added under stirring, and the mixture is kept cool for 0.5 h and then at room temperature for 2 h. The reaction mixture is poured on a mixture of 300 g of ice, 70 ml of water, and 130 ml of concentrated hydrochloric acid. The precipitate formed is filtered off, washed with water, dried, and washed with ether. Recrystallization from ethylacetate yields 27.5 h og sulfonamide melting at 163°–165° C. Yield 68% of theoretical.

Calculated for $C_{14}H_{18}N_2O_4S$: C=54.2, H=5.8, N=9.0, S=10.3, Obtained: C=54.2, H=5.9, N=9.1, S=10.3.

EXAMPLE 9

2-Phthalimidoethanesulfone pyrrolidide

Of 6.48 g of 2-phthalimidoethane sulfonylchloride, about half the quantity is added to a mixture of 40 ml of acetonitrile and 2.1 ml of pyrrolidine; the temperature rises to 42° C. Another 2.1 ml of pyrrolidine is added, and the temperature rises to 48° C. The remaining 2-phthalimidoethane sulfonylchloride is added. When the reaction begins to slacken, the mixture is heated under reflux for 2.5 h, after which it is cooled and filtered. Water is added, and the precipitate formed is filtered off. Recrystallization from ethylacetate yields 2.97 g of amide, melting at 176°–178° C. Yield 39% of theoretical.

Calculated for $C_{14}H_{16}N_2O_4S$: C=54.5, H=5.2, N=9.1, S=10.4, Obtained: C=54.4, H=5.2, N=9.1, S=10.4.

EXAMPLE 10

2-Phthalimidoethanesulfone pyrrolidide

Alternatively, 2-phthalimidoethanesulfone pyrrolidide may be prepared in the following way:

A mixture of 1.27 g of 2-phthalimidoethane sulfonamide, 0.6 ml of 1.4-dibromobutane, 1.38 g of potassium carbonate, 10 ml of acetonitrile and about 0.05 g of potassium iodide is heated for 37 h under reflux and stirring, after which there is added to the reaction mixture 25 ml of water, 5 ml of 3N hydrochloric acid and 15 ml of methylene chloride. The organic phase is separated and treated first with 15 ml of 3N sodium carbonate then with water, dried, and evaporated. After washing with ethanol and recrystallization, 0.74 g of pyrrolidide is obtained; m.p. 177°–179° C. Yield 51% of theoretical.

EXAMPLE 11

2-Phthalimidoethanesulfone methylamide

A mixture of 1.27 g of 2-phthalimidoethane sulfonamide, 0.30 ml of dimethyl sulfate, 0.35 g of potassium carbonate and 10 ml of acetonitrile is heated under stirring and reflux. After 0.5 h there is added 0.18 ml of dimethyl sulfate. The mixture is allowed to react for another hour, after which 20 ml of water, 5 ml of 3N hydrochloric acid and 15 ml of methylene chloride are added. The organic phase is treated with sodium carbonate solution and water, dried, and evaporated. Recrystallization from ethanol yields 0.39 g of sulfonamide, melting at 139°–141° C. Yield 31% of theoretical.

The anticonvulsive effect of the compounds was studied on three types of experimental epilepsy. Convulsions were induced in mice by subcutaneous administration of pentylene tetrazole or strychnine, or by electrical stimulation with a 50 mA current (E. A. Swinyard, Assay of antiepileptic drug activity in experimental animals: Standard tests in International Enocyclopedica of Pharmacology and Therapeutics, Section 19, vol 1: Anticonvulsant Drugs, 1972). Several compounds protected against convulsions in all three tests after oral as well as intraperitoneal administration. $ED_{50}$ (the dose effective in 50% of the treated animals) ranged from 103 mg/kg to >300 mg/kg (table I). No sedative effect could be observed.

TABLE I

Antiepileptic screening

| Compound | Anticonvulsive activity | | |
|---|---|---|---|
| | $ED_{50}$ MES | mg/kg MET | i.p. STR |
| 2-Phthalimidoethanesulfone amide | 122 | >300 | 93 |
| 2-Phthalimidoethanesulfone tert-butylamide | >300 | >300 | — |
| 2-Phthalimidoethanesulfone pyrrolidide | >300 | >300 | — |
| 2-Phthalimidoethanesulfonyl acetamide | >300 | >300 | — |
| 2-Phthalimidoethanesulfone methylamide | 112 | 170 | 189 |
| 2-Phthalimidoethanesulfone dimethylamide | 113 | 231 | 234 |
| 2-Phthalimidoethanesulfone n-butylamide | 219 | >300 | — |
| 2-Phthalimidoethanesulfone ethylamide | 103 | 138 | 126 |
| 2-Phthalimidoethanesulfone isopropylamide | 130 | >300 | 227 |
| 2-Phthalimidoethanesulfone n-propylamide | 252 | >300 | >300 |

MES = maximal electroshock test
MET = metrazole (= pentylene tetrazole) convulsant threshold test.
STR = strychnine convulsant threshold test Isolated perfused rat heart, prepared after the method of Langendorff, and isolated spontaneously beating rat atria (W. C. Holland & J. H. Burn, J. Brit. Med., vol 1, 1031, 1958) were used for studies of the antiarrhythmic effect of the compounds. Arrhythmia was induced by $K^+$ deficiency and by aconitine. A clear antiarrhythmic effect was demonstrated (tables II and III). Some of the compounds had a better effect than the reference substances lidocaine, quinidine, and propranolol. Besides the above-described in vitro tests, an in vivo method was used: the antiarrhythmic effect of the compounds was studied in quineapigs with ouabain-induced arrhythmia. When the quinea-pigs had been treated with the new compounds, larger doses of ouabain were required to induce arrhythmia (table IV). Propranolol, which was used as a reference substance in test, caused bradycardia, which the test substances did not.

TABLE II

Effect of the test compounds on arrhythmia induced by $K^+$ deficiency in perfused Langendorff's rat heart.

| Compound | N | Conc. M | Development of arrhythmia. Percentage change in time |
|---|---|---|---|
| Lidocaine | 5 | $10^{-4}$ | +30,9 |
| 2-Phthalimidoethanesulfone amide | 3 | " | +23,6 |
| 2-Phthalimidoethanesulfone tert-butylamide | 3 | " | +8,5 |
| 2-Phthalimidoethanesulfone pyrrolidide | 3 | " | +0,2 |
| 2-Phthalimidoethanesulfonyl acetamide | 3 | " | +26,3 |
| 2-Phthalimidoethanesulfone methylamide | 3 | " | +22,7 |
| 2-Phthalimidoethanesulfone dimethylamide | 2 | " | −5,1 |
| 2-Phthalimidoethanesulfone n-butylamide | 4 | " | +4,9 |
| 2-Phthalimidoethanesulfone ethylamide | 2 | " | −4,7 |
| 2-Phthalimidoethanesulfone isopropylamide | 2 | " | −10,1 |
| 2-Phthalimidoethanesulfone n-propylamide | 3 | " | +10,3 |

TABLE III

Ability of the test compounds to protect against development of arrhythmia in spontaneously beating isolated rat atria after addition of $2.5 \times 10^{-5}$ M aconitine.

| Compound | N | Conc. M | Development of arrhythmia Time in seconds ± SE | Δ sec. |
|---|---|---|---|---|
| Control | 8 | — | | |
| Quinidine | 3 | $5 \times 10^{-4}$ | 267 ± 71 | +71 |
| " | 7 | $1 \times 10^{-4}$ | 450 ± 59 | +243 |
| " | 2 | $5 \times 10^{-5}$ | 225 ± 20 | +18 |
| Propranolol | 2 | $5 \times 10^{-4}$ | 105 ± 50 | −102 |
| " | 3 | $1 \times 10^{-4}$ | 325 ± 16 | +118 |
| " | 3 | $5 \times 10^{-5}$ | 301 ± 80 | +94 |
| " | 2 | $1 \times 10^{-5}$ | 245 ± 50 | +38 |
| Lidocaine | 2 | $5 \times 10^{-4}$ | 95 ± 45 | −112 |
| " | 2 | $1 \times 10^{-4}$ | 295 ± 75 | +88 |
| " | 2 | $5 \times 10^{-5}$ | 335 ± 5 | +128 |
| " | 2 | $1 \times 10^{-5}$ | 200 ± 35 | −7 |
| 2-Phthalimidoethanesulfone amide | 3 | $5 \times 10^{-4}$ | 397 ± 86 | +190 |
| 2-Phthalimidoethanesulfone amide | 3 | $1 \times 10^{-4}$ | 222 ± 76 | +15 |
| 2-Phthalimidoethanesulfone methylamide | 2 | $1 \times 10^{-3}$ | >900 | >+693 |
| 2-Phthalimidoethanesulfone methylamide | 3 | $5 \times 10^{-4}$ | 420 ± 53 | +213 |
| 2-Phthalimidoethanesulfone methylamide | 3 | $1 \times 10^{-4}$ | 445 ± 85 | +238 |
| 2-Phthalimidoethanesulfone methylamide | 3 | $5 \times 10^{-5}$ | 290 ± 52 | +83 |
| 2-Phthalimidoethanesulfone dimethylamide | 2 | $5 \times 10^{-4}$ | 222 ± 50 | +15 |
| 2-Phthalimidoethanesulfone dimethylamide | 3 | $1 \times 10^{-4}$ | 143 ± 38 | −64 |
| 2-Phthalimidoethanesulfone dimethylamide | 2 | $5 \times 10^{-5}$ | 217 ± 50 | +10 |
| 2-Phthalimidoethanesulfone ethylamide | 3 | $1 \times 10^{-4}$ | 751 ± 49 | +544 |
| 2-Phthalimidoethanesulfone ethylamide | 3 | $7,5 \times 10^{-5}$ | 326 ± 171 | +119 |
| 2-Phthalimidoethanesulfone ethylamide | 3 | $5 \times 10^{-5}$ | 160 ± 55 | −47 |
| 2-Phthalimidoethanesulfone n-propylamide | 3 | $5 \times 10^{-4}$ | 441 ± 59 | +234 |
| 2-Phthalimidoethanesulfone n-propylamide | 4 | $1 \times 10^{-4}$ | 488 ± 45 | +281 |
| 2-Phthalimidoethanesulfone n-propylamide | | $5 \times 10^{-5}$ | 278 ± 94 | +71 |
| 2-Phthalimidoethanesulfone isopropylamide | 4 | $1 \times 10^{-4}$ | >900 | >+693 |
| 2-Phthalimidoethanesulfone isopropylamide | 3 | $5 \times 10^{-5}$ | 676 ± 27 | +469 |
| 2-Phthalimidoethanesulfone isopropylamide | | $1 \times 10^{-5}$ | 225 ± 17 | +18 |
| 2-Phthalimidoethanesulfone n-butylamide | 3 | $1 \times 10^{-3}$ | >900 | >+693 |
| 2-Phthalimidoethanesulfone n-butylamide | 3 | $5 \times 10^{-4}$ | 508 ± 120 | +301 |
| 2-Phthalimidoethanesulfone n-butylamide | 3 | $1 \times 10^{-4}$ | 258 ± 114 | +51 |
| 2-Phthalimidoethanesulfonyl acetamide | 4 | $5 \times 10^{-4}$ | 246 ± 74 | +39 |
| 2-Phthalimidoethanesulfonyl acetamide | 3 | $1 \times 10^{-4}$ | 192 ± 36 | −15 |

TABLE IV

Ability of the test compounds to protect against development of arrhythmia in guinea-pigs after infusion of ouabain 20 μg/kg/min.

| Compound | N | Dose mg/kg iv | HR, beats/min. ± SE O-value | HR, beats/min. ± SE 5 min. after adm. of test compound | Ouabain dose, μg/kg ± SE, inducing arrhythmia | Ouabain dose, μg/kg ± SE, inducing asystole |
|---|---|---|---|---|---|---|
| Control | 13 | — | 326 ± 10 | — | 175 ± 7 | 289 ± 11,1 |
| Propranolol | 3 | 1 | 280 ± 17 | 219 ± 7 | 240 ± 5.x.x | 363 ± 11.x.x |
| | 3 | 3 | 293 ± 17 | 238 ± 14 | 295 ± 35.x | 435 ± 24.x.x |
| | 5 | 6 | 301 ± 10 | 206 ± 6 | 269 ± 39.x | 418 ± 34.x |
| Phthalimidoethanesulfone amide | 1 | 12 | 333 | 330 | 170 | 220 |
| Phthalimidoethanesulfone methylamide | 2 | 6 | 261 ± 45 | 255 ± 51 | 188 ± 17 | 345 ± 20 |
| | 2 | 12 | 369 ± 30 | 399 ± 22 | 195 ± 15 | 265 ± 50 |
| Phthalimidoethanesulfone ethylamide | 2 | 3 | 332 ± 22 | 332 ± 16 | 175 ± 5 | 318 ± 22 |
| | 1 | 6 | 285 | 270 | 150 | 360 |
| Phthalimidoethanesulfone n-propylamide | 2 | 2 | 229 ± 34 | 243 ± 18 | 165 ± 10 | 272 ± 27 |
| | 2 | 3 | 286 ± 55 | 294 ± 45 | 160 ± 10 | 322 ± 62 |
| Phthalimidoethanesulfone isopropylamide | 2 | 3 | 321 ± 39 | 312 ± 27 | 197 ± 32 | 297 ± 27 |
| | 1 | 6 | 303 | 291 | 155 | 290 |
| Phthalimidoethanesulfone n-butylamide | 1 | 3 | 210 | 213 | 175 | 340 |
| | 2 | 6 | 256 ± 19 | 256 ± 43 | 200 ± 0.x | 382 ± 37 |
| Phthalimidoethanesulfonyl acetamide | 2 | 1 | 292 ± 1 | 316 ± 10 | 185 ± 5 | 307 ± 2 |

TABLE IV-continued

| Ability of the test compounds to protect against development of arrhythmia in guinea-pigs after infusion of ouabain 20 μg/kg/min. | | | | | | |
|---|---|---|---|---|---|---|
| | | | HR, beats/min. ± SE | | Ouabain dose, μg/kg ± SE, inducing | |
| Compound | N | Dose mg/kg iv | O-value | 5 min. after adm. of test compound | arrhythmia | asystole |
| | 3 | 3 | 260 ± 9 | 259 ± 10 | 215 ± 24 | 355 ± 20$^x$ |
| | 4 | 6 | 329 ± 15 | 334 ± 11 | 212 ± 16 | 345 ± 26 |
| | 5 | 12 | 329 ± 19 | 349 ± 19 | 210 ± 16 | 360 ± 13$^x$ |

$^x p < 0.05$
$^{xx} p < 0.01$

The effects of the compounds on the CNS were studied in mice. The rotating rod method (N. W. Dunham and T. S. Miya, J. Am. Pharm. Assoc. 54, 208, 1957) was used for studying motor coordination. For all the tested compounds $TD_{50}$ (the dose at which 50 percent of the animals fell off the rod) was always higher than the anticonvulsive $ED_{50}$ (the dose preventing convulsions in 50 percent of the animals). Although no sedative effect could be observed in these tests, hexobarbiturate-induced sleep was prolonged in mice after administration of those test compounds which were found to have an anticonvulsive action. 2-Phthalimidoethane sulfonylacetamide, which had an antiarrhythmic but no anticonvulsive effect, did not prolong the time of sleep.

The hot plate method (P. A. J. Janssen & A. Jagenau, J. Pharm. Pharmacol. 13, 513, 1957) did not reveal any analgesic effect on mice. The test compounds had no diuretic effect on unanesthetized rats nor any effect on the blood circulation in normotensive uretane-anesthetized rats. The compounds were found to be atoxic; $LD_{50}$ in mice after oral administration was >2 g/kg.

I claim:

1. A method of treating epilepsy in a mammal afflicted therewith, said method comprising administering to said mammal a therapeutically effective amount of a compound with the chemical structure:

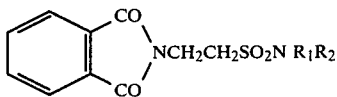

where $R_1 = H$
$R_2 =$ ethyl-,n-propyl-,isopropyl, or n-butyl
or where

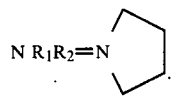

2. A method according to claim 1 wherein said compound is administered orally or intraperitoneally.

3. A method of treating arrythmia in a mammal afflicted therewith, said method comprising administering to said mammal a therapeutically effective amount of a compound with the chemical structure:

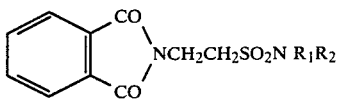

where
$R_1 = H$
$R_2 =$ ethyl-,n-propyl-,isopropyl, or n-butyl
or where

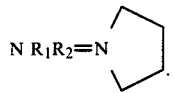

4. A method according to claim 3 wherein said compound is administered intravenously.

* * * * *